(12) United States Patent
Ameri et al.

(10) Patent No.: US 8,666,513 B2
(45) Date of Patent: Mar. 4, 2014

(54) IMPLANTABLE LEAD WITH SHIELDING

(75) Inventors: Masoud Ameri, Maple Plain, MN (US); Arthur J. Foster, Centerville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 984 days.

(21) Appl. No.: 12/328,515

(22) Filed: Dec. 4, 2008

(65) Prior Publication Data
US 2009/0149934 A1 Jun. 11, 2009

Related U.S. Application Data (60) Provisional application No. 60/992,874, filed on Dec. 6, 2007.

(51) Int. Cl.
*A61N 1/372* (2006.01)

(52) U.S. Cl.
USPC .......................................... 607/122; 607/119

(58) Field of Classification Search
USPC .......................................... 607/116, 119, 122
See application file for complete search history.

(56) References Cited

U.S. PATENT DOCUMENTS

| | | | |
|---|---|---|---|
| 4,131,759 A | 12/1978 | Felkel | |
| 4,484,586 A | 11/1984 | McMickle et al. | |
| 5,554,139 A | 9/1996 | Okajima | |
| 5,800,496 A | 9/1998 | Swoyer et al. | |
| 5,954,760 A * | 9/1999 | Jarl | 607/122 |
| 6,143,013 A | 11/2000 | Samson et al. | |
| 6,671,554 B2 | 12/2003 | Gibson et al. | |
| 6,876,886 B1 | 4/2005 | Wang | |
| 6,980,865 B1 | 12/2005 | Wang et al. | |
| 7,013,180 B2 | 3/2006 | Villaseca et al. | |
| 7,123,013 B2 | 10/2006 | Gray | |
| 7,138,582 B2 | 11/2006 | Lessar et al. | |
| 7,174,219 B2 | 2/2007 | Wahlstrand et al. | |
| 7,174,220 B1 | 2/2007 | Chitre et al. | |
| 7,388,378 B2 | 6/2008 | Gray et al. | |

(Continued)

FOREIGN PATENT DOCUMENTS

| | | |
|---|---|---|
| EP | 0092798 A1 | 11/1983 |
| JP | 58192205 A | 11/1983 |

(Continued)

OTHER PUBLICATIONS

International Search Report and Written Opinion issued in PCT/US2008/087068 on Aug. 3, 2009.

(Continued)

*Primary Examiner* — Joseph Dietrich
(74) *Attorney, Agent, or Firm* — Faegre Baker Daniels LLP (57) ABSTRACT

Medical device leads with magnetic shielding and methods of shielding medical device leads from magnetic fields during medical procedures such as magnetic resonance imaging (MRI) are described. An illustrative implantable medical device includes a lead including a lead conductor having a length and a helically coiled ribbon shield radially surrounding the lead conductor along at least a portion of the length of the lead. The ribbon shield can include one or more inner ribbon conductors and/or one or more outer ribbon conductors. The outer ribbon conductor can have a variable width (e.g., a necked-down configuration, an arrowhead configuration, or an undulating configuration) along the length of the lead. In some cases, the helically coiled ribbon has a variable pitch along the length of the lead that may be the same as or different from that of the lead conductor pitch.

21 Claims, 13 Drawing Sheets

(56) References Cited

U.S. PATENT DOCUMENTS

| | | | |
|---|---|---|---|
| 7,410,485 B1 * | 8/2008 | Fink et al. | 606/33 |
| 7,551,966 B2 | 6/2009 | MacDonald | |
| 8,244,346 B2 | 8/2012 | Foster et al. | |
| 2003/0083723 A1 | 5/2003 | Wilkinson et al. | |
| 2003/0083726 A1 | 5/2003 | Zeijlemaker et al. | |
| 2003/0140931 A1 | 7/2003 | Zeijlemaker et al. | |
| 2003/0144705 A1 | 7/2003 | Funke | |
| 2003/0144718 A1 | 7/2003 | Zeijlemaker | |
| 2003/0144719 A1 | 7/2003 | Zeijlemaker | |
| 2003/0144720 A1 | 7/2003 | Villaseca et al. | |
| 2003/0144721 A1 | 7/2003 | Villaseca et al. | |
| 2003/0204217 A1 | 10/2003 | Greatbatch | |
| 2004/0162600 A1 | 8/2004 | Williams | |
| 2004/0210289 A1 | 10/2004 | Wang et al. | |
| 2005/0065587 A1 | 3/2005 | Gryzwa | |
| 2005/0113676 A1 | 5/2005 | Weiner et al. | |
| 2005/0113873 A1 | 5/2005 | Weiner et al. | |
| 2005/0113876 A1 | 5/2005 | Weiner et al. | |
| 2005/0222656 A1 | 10/2005 | Wahlstrand et al. | |
| 2005/0222657 A1 | 10/2005 | Wahlstrand et al. | |
| 2005/0222658 A1 | 10/2005 | Hoegh et al. | |
| 2005/0222659 A1 | 10/2005 | Olsen et al. | |
| 2005/0247472 A1 | 11/2005 | Helfer et al. | |
| 2005/0283167 A1 | 12/2005 | Gray | |
| 2006/0030774 A1 | 2/2006 | Gray et al. | |
| 2006/0041294 A1 | 2/2006 | Gray | |
| 2006/0247747 A1 | 11/2006 | Olsen et al. | |
| 2006/0247748 A1 | 11/2006 | Wahlstrand et al. | |
| 2006/0271138 A1 | 11/2006 | MacDonald | |
| 2007/0106332 A1 | 5/2007 | Denker et al. | |
| 2007/0179577 A1 | 8/2007 | Marshall et al. | |
| 2007/0179582 A1 | 8/2007 | Marshall et al. | |
| 2007/0191914 A1 | 8/2007 | Stessman | |
| 2008/0033497 A1 | 2/2008 | Bulkes et al. | |
| 2008/0132985 A1 | 6/2008 | Wedan et al. | |
| 2008/0195186 A1 | 8/2008 | Li et al. | |
| 2008/0262584 A1 | 10/2008 | Bottomley et al. | |
| 2009/0149920 A1 | 6/2009 | Li et al. | |
| 2009/0171421 A1 | 7/2009 | Atalar et al. | |
| 2010/0036466 A1 | 2/2010 | Min et al. | |
| 2012/0130453 A1 | 5/2012 | Stahmann et al. | |
| 2012/0323297 A1 | 12/2012 | Li et al. | |

FOREIGN PATENT DOCUMENTS

| | | |
|---|---|---|
| JP | 8308934 A | 11/1996 |
| JP | 2003047653 A | 2/2003 |
| JP | 2004141679 A | 5/2004 |
| JP | 2005515854 A | 6/2005 |
| WO | WO2005081784 A2 | 9/2005 |
| WO | WO 2007/047966 | 4/2007 |

OTHER PUBLICATIONS

International Search Report and Written Opinion issued in PCT/US2008/085533, mailed Aug. 26, 2010.

Invitation to Pay Additional Fees and, Where Applicable, Protest Fee dated Aug. 17, 2009 from PCT Application No. PCT/US2008/085533.

International Search Report and Written Opinion of the International Searching Authority, PCT/US2008/085518, Oct. 29, 2009.

International Search Report and Written Opinion issued in PCT/US2011/052684, mailed Jan. 25, 2012, 11 pages.

* cited by examiner

IMPLANTABLE LEAD WITH SHIELDING

CROSS-REFERENCE TO RELATED APPLICATION

This application claims the benefit of U.S. Provisional Application No. 60/992,874, filed on Dec. 6, 2007, which is hereby incorporated by reference in its entirety for all purposes.

TECHNICAL FIELD

Various embodiments of the present invention relate to medical devices and the simultaneous delivery of diagnostic and therapeutic treatments. More specifically, embodiments of the present invention relate to medical devices with magnetic shielding and methods of shielding medical devices from magnetic fields during medical procedures such as magnetic resonance imaging (MRI).

BACKGROUND

Magnetic resonance imaging (MRI) is a non-invasive imaging method that utilizes nuclear magnetic resonance techniques to render images within a patient's body. Typically, MRI systems employ the use of a magnetic coil having a magnetic field strength of between about 0.2 to 3 Teslas. During the procedure, the body tissue is briefly exposed to RF pulses of electromagnetic energy in a plane perpendicular to the magnetic field. The resultant electromagnetic energy from these pulses can be used to image the body tissue by measuring the relaxation properties of the excited atomic nuclei in the tissue.

During imaging, the electromagnetic radiation produced by the MRI system may be picked up by implantable device leads used in implantable medical devices such as pacemakers or cardiac defibrillators. This energy may be transferred through the lead to the electrode in contact with the tissue, which may lead to elevated temperatures at the point of contact. The degree of tissue heating is typically related to factors such as the length of the lead, the conductivity or impedance of the lead, and the surface area of the lead electrodes. Exposure to a magnetic field may also induce an undesired voltage in the lead.

SUMMARY

Medical device leads with magnetic shielding and methods of shielding medical device leads from magnetic fields during medical procedures such as magnetic resonance imaging (MRI) are described. Some embodiments provide for an implantable medical device, comprising a lead including a lead conductor having a length and a helically coiled ribbon shield radially surrounding the lead conductor along at least a portion of the length of the lead. In some embodiments, the ribbon shield is configured to dissipate electromagnetic energy received by the lead during a magnetic resonance imaging procedure.

In accordance with various embodiments, the ribbon shield can include one or more inner ribbon conductors and/or one or more outer ribbon conductors (e.g., a plurality of wire conductors). The outer ribbon conductors, in some embodiments, can be disposed about the one or more inner ribbon conductors. In some embodiments, the outer ribbon conductor can have a variable width (e.g., a necked-down configuration, an arrowhead configuration, or an undulating configuration) along the length of the lead. In some embodiments, the helically coiled ribbon has a variable pitch (e.g., sinusoidal function, a modified square-wave function, continuously changing pitch, or a pitch changing at only a finite number of locations) along the length of the lead.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the scope of the present invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
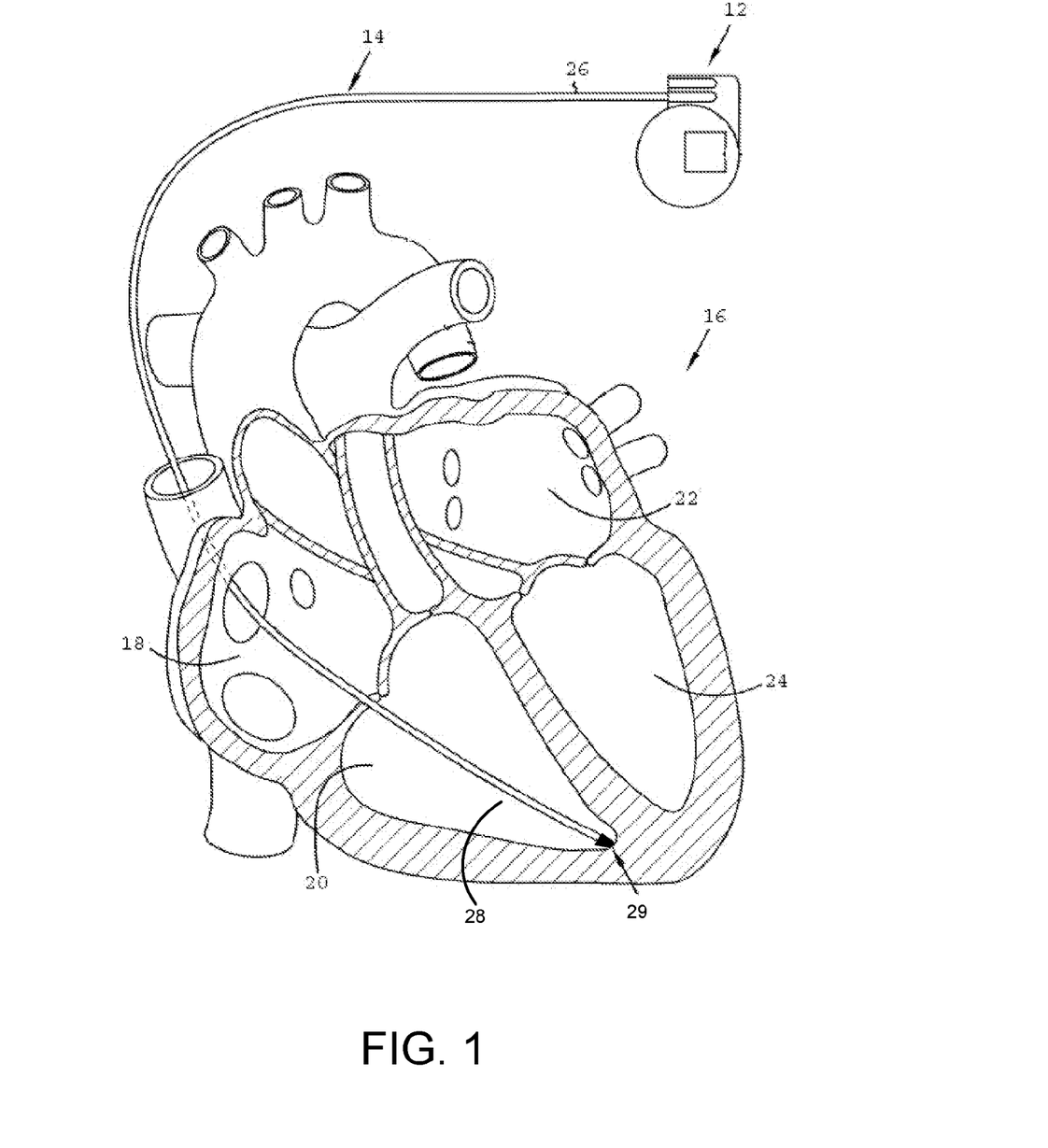
FIG. 1 is a schematic view of an illustrative medical device having a lead implanted within the body of a patient.

FIG. 1 is a schematic view of an illustrative medical device 12 equipped with a lead implanted within the body of a patient. In the illustrative embodiment depicted, the medical device 12 comprises a pulse generator implanted within the body. The medical device 12 includes a lead 14 placed in the patient's heart 16. The heart 16 includes a right atrium 18, a right ventricle 20, a left atrium 22, and a left ventricle 24. The pulse generator 12 can be implanted subcutaneously within the body, typically at a location such as in the patient's chest or abdomen, although other implantation locations are possible.

A proximal portion 26 of the lead 14 can be coupled to or formed integrally with the pulse generator 12. A distal portion 28 of the lead 14, in turn, can be implanted within a desired location within the heart 16 such as the right ventricle 20, as shown, and can include an electrode 29 that supplies therapeutic energy for pacing the heart 16 and/or for sensing electrical activity occurring within the heart 16. Although the illustrative embodiment depicts only a single lead 14 inserted into the patient's heart 16, it should be understood, however, that multiple leads can be utilized so as to electrically stimulate other areas of the heart 16. In some embodiments, for example, the distal portion of a second lead (not shown) may be implanted in the right atrium 18. In addition, or in lieu, another lead may be implanted at the left side of the heart 16 (e.g., in the coronary veins) to stimulate the left side of the heart 16. Other types of leads such as epicardial leads may also be utilized in addition to, or in lieu of, the lead 14 depicted in FIG. 1.

During operation, the lead 14 can be configured to convey electrical signals between the heart 16 and the pulse generator 12. For example, in those embodiments where the pulse generator 12 is a pacemaker, the lead 14 can be utilized to deliver electrical therapeutic stimulus for pacing the heart 16. In those embodiments where the pulse generator 12 is an implantable cardiac defibrillator, the lead 14 can be utilized to deliver electric shocks to the heart 16 in response to an event such as a heart attack. In some embodiments, the pulse generator 12 includes both pacing and defibrillation capabilities.

Figure 2:
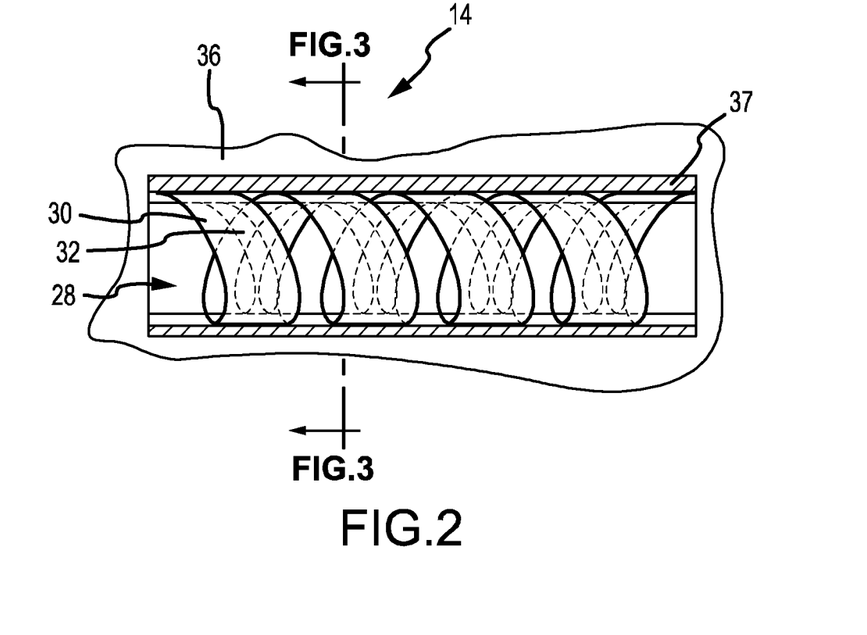
FIG. 2 is a view showing a portion of the lead of FIG. 1 in greater detail.

FIG. 2 is a view showing a portion of the lead 14 of FIG. 1 in greater detail. In some embodiments, and as shown in FIG. 2, the lead 14 includes a helix-shaped shielding ribbon 30 disposed about an inner conductor 32 of the lead 14. The ribbon 30 may extend along all or a portion of the length of the lead 14, and is configured to at least in part radially surround the conductor 32 to prevent RF electromagnetic waves generated by an MRI scanner from heating the tissue at the electrode point of contact to the tissue. The ribbon 30 may also serve other purposes such as reducing the stress on the lead 14 when bent or stretched, and providing additional reduction in electrical interferences from the MRI scanner or other sources of electromagnetic interference.

In certain embodiments, the lead 14 further includes a layer of insulation 37 disposed about all or a portion of the ribbon 30 to further prevent electrical energy generated by the presence of a gradient field from entering into the tissue 36 surrounding the lead 14.

Figure 3:
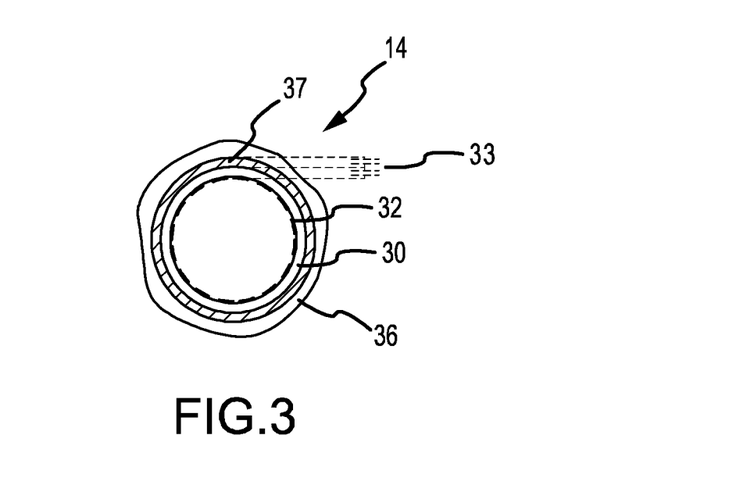
FIG. 3 is a transverse view of the lead of FIG. 2.

Various parameters of the shielding ribbon 30 can be configured so as to maximize the impedance path along the length of the lead 14 while also providing a low impedance path from the shield to the surrounding tissue 36 and coupling back the induced voltage to the surrounding tissue which is being dissipated in the tissue along the length of the lead. Examples of ribbon parameters can include, but are not limited to, the width of the ribbon 30, the pitch of the ribbon 30, the thickness of the ribbon 30, and the material properties of the ribbon 30. In some embodiments, the wide surface area of the width of the ribbon 30 is configured so as to provide maximum coverage of the lead 14, which prevents the electromagnetic field from reaching the enclosed lead conductor surface as shown further in conjunction with FIG. 3.

During the operation of the MRI scanner, RF energy can be picked up by the lead creating a voltage potential 33 between the conductor 32 and ribbon 30 and a second voltage potential between ribbon 30 and insulation 37. More specifically, the tangential components of the electrical field along the length of the lead 14 are being integrated by the conductors, creating a voltage potential along the length of the lead 14. In accordance with some embodiments, the outer conductor shields the inner conductor(s) from this electric field. The voltage along the length of the lead 14 need not be uniform as in circuits where the dimensions of the circuit are much shorter than wavelength. Moreover, the shape of the distribution of the voltage potentials depends on factors including, but not limited to, characteristic impedance of the lead and surrounding tissue, geometries, frequency, etc. According to various embodiments, the choice of the width of the ribbon 30, the materials used in the conductor 32, ribbon 30, and insulation 37, pitch of the conductor 32, pitch of the ribbon 30 as well as other parameters can affect the voltage between these layers of the lead 14.

Figure 4:
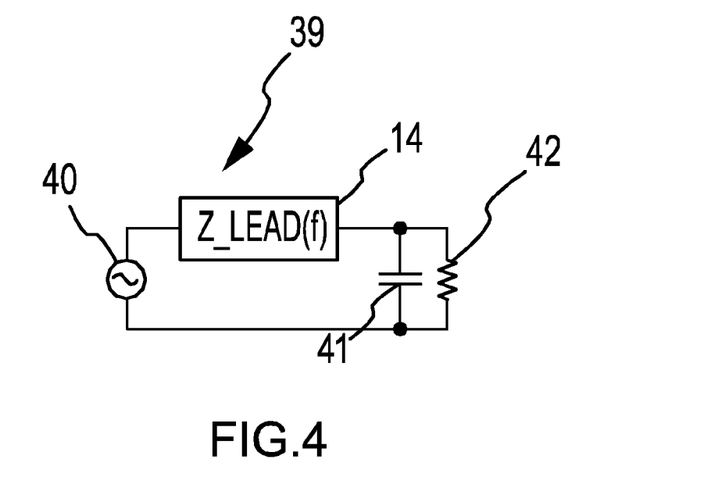
FIG. 4 is a schematic view showing a simplified equivalence circuit for the lead of FIG. 1.

The inductance of a helix ribbon (such as ribbon 30 shown in FIG. 2) in conjunction with the capacitance between its winding turns forms a resonance circuit 39 along the length of the helix. This can be seen, for example, in FIG. 4, which shows the RF energy picked up on the lead 14 from the electromagnetic field produced by the MRI, which can be represented in the circuit 39 as voltage source 40. FIG. 4 represents a very simple model to express the ideas. For circuits with geometries comparable to wavelength of the signal, the lump model is not sufficient and distributed model representation may be needed.

As further represented in the circuit 39, the lead 14 has an equivalent impedance (i.e., inductance in parallel with capacitance which creates a resonance circuit) at the frequency of the MRI device, as indicated generally by "Z_lead (f)." At resonance the impedance of Z_lead(f) is maximized in some embodiments. The impedance of the electrode 29 contact to the tissue likewise has an equivalent impedance, as indicated generally by resistor 42. Capacitor 41, in turn, may represent the capacitive coupling of lead 14 to surrounding tissue along the length of the lead 14, which is a path for the high frequency current (energy) to leak into the surrounding tissue at the RF frequency of the MRI scanner.

The parameters of the ribbon 30 can be varied such that the impedance of the helix along its axis is maximized at RF frequencies exhibited in an MRI environment. The outer diameter of the shield of some embodiments can be between approximately 30-100 mils. In some embodiments, the width of the shield can be between approximately 4-15 mils. The thickness of the shield in various embodiments can be between approximately 1-10 mils. In some embodiments, the separation between the shield turns can be less than or equal to 1 mil. In other embodiments, the outer diameter of the shield, width of the shield, thickness of the shield, and/or separation between the shield turns can be smaller or larger than those ranges indicated above. In some embodiments, the shield material can be MP35N or other materials. The relative dielectric constant of insulating material can be between approximately 2-10 in accordance with some embodiments. However, in other embodiments, the dielectric constant can be smaller or larger.

Some embodiments provide that the insulation thickness between the shield and surrounding tissue should be as small as possible. If a silicon or polypropylene is used, for example, this range can be less than 10 mils. Other techniques that can maximize this capacitance coupling can be used in accordance with various embodiments. Examples include, but are not limited to, coating the shield and/or use of a higher dielectric constant material for insulation.

Figure 5:
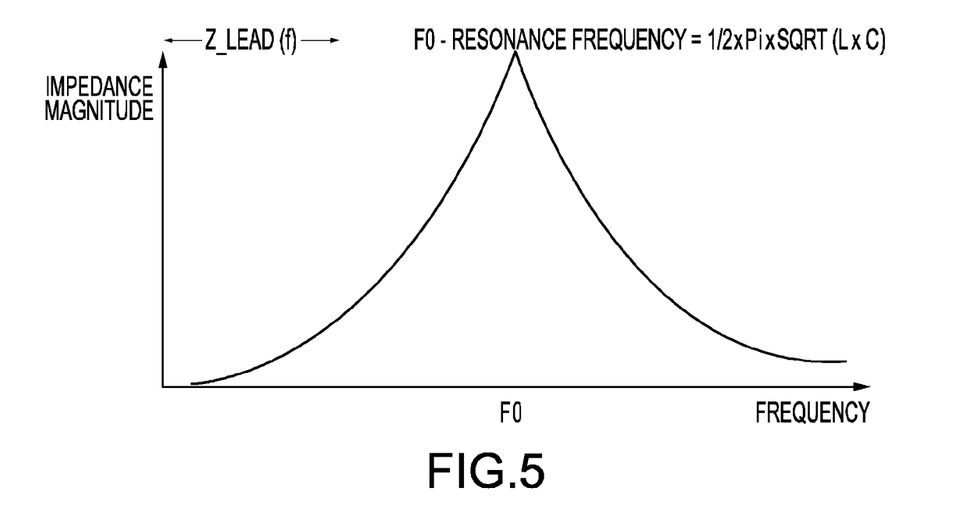
FIG. 5 is a graph showing the impedance magnitude of the lead versus RF frequency in an MRI environment.

This can be seen, for example, in FIG. 5, which shows a dramatic increase in the impedance magnitude at resonance frequency "F0". The resonance frequency of an equivalent inductor and capacitance in parallel is $1/2\pi\sqrt{LC}$.

In use, the relatively high impedance path provided by the ribbon 30 prevents propagation of the electromagnetic energy through the length of the ribbon 30. At the same time, the relatively wide width of the ribbon 30, in conjunction with a very thin insulator layer 37 in some embodiments, can produce a very low impedance-capacitive coupling to the surrounding tissue 36. One reason for having a low impedance is to couple the absorbed energy to the surrounding tissue. As a result, this prevents propagation of energy along the length of the lead, minimizing concentration of the energy at electrode 29 that is in contact with the tissue. If the shield is not insulated, as shown in one alternative embodiment depicted, for example, in FIG. 6, there is a very low impedance-resistive path to the surrounding tissue 36. This low impedance path couples back picked up energy to surrounding tissue which dissipates the picked-up RF energy in tissue along the length of the lead 14.

Figure 6:
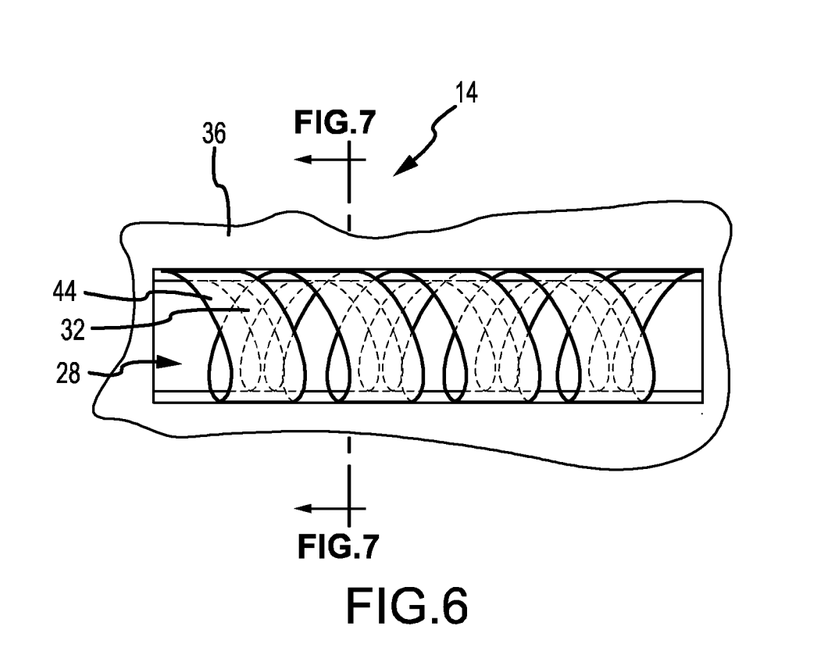
FIG. 6 is a view showing a portion of a lead in accordance with another illustrative embodiment.
Figure 7:
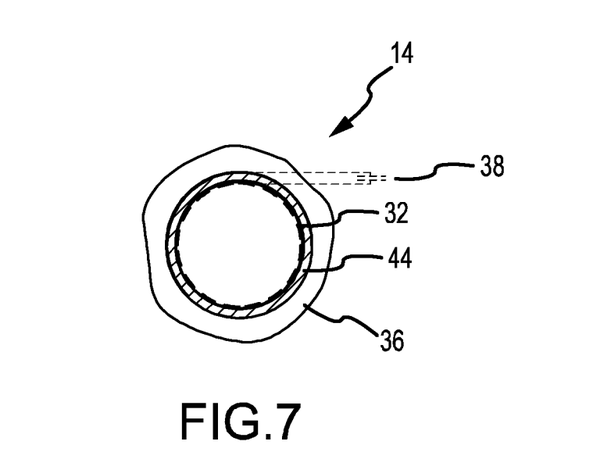
FIG. 7 is a transverse view of the lead of FIG. 6.

FIGS. 6-7 are views showing a portion 28 of a lead 14 in accordance with an alternative embodiment having an un-insulated shielding ribbon. The illustrative embodiment of FIG. 6 is similar to that depicted in FIGS. 2-3, including a helix-shaped shielding ribbon 44 disposed about the inner conductor 32 of the lead 14. In the embodiment of FIG. 6, there is no insulated layer between the shielding ribbon 44 and the surrounding tissue 36. In use, this configuration provides a very low impedance path to the surrounding tissue 36, which, during magnetic resonance imaging, aids in coupling back the picked up energy to surrounding tissue along the length of the lead 14. A voltage potential 38 is created when lead 14 picks up RF energy from the MRI scanner.

In some embodiments, dissipation of energy along the length of shield is also possible. For example, the shielding material can be chosen in such a way that the thickness of shield is about four times the skin depth of the material. The overall resistance of the shield, in some embodiments, can be chosen to be on the order of a magnitude more than the inner conductor. Since the cross section of the ribbon shield is much larger than the inner leads, the resistivity of the material should be much higher because resistance=resistivity× length/cross section area.

Figure 8:
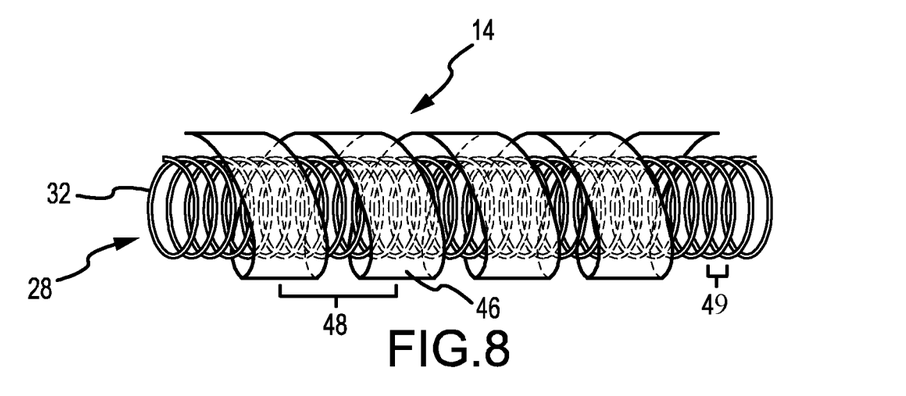
FIG. 8 is a view showing a portion of a lead in accordance with another illustrative embodiment.

FIG. 8 is a view showing a portion of a lead 14 in accordance with another illustrative embodiment. In the illustrative embodiment of FIG. 8, the lead 14 includes a helix-shaped shielding ribbon 46 that is loosely wound about the inner conductor 32 of the lead 14. In some embodiments, the ribbon 46 may be wound helically about the inner conductor 32. In these embodiments, the helical construction of the shield can be used to take advantage of the inductance of the helical construction. If the shield has low impedance along the length of the lead, then the picked up energy by the shield itself propagates along the length of the lead which, in turn, could cause heating at the end of the lead directly, or by coupling back to the inner lead near the electrode area. The electric field near the end of the lead increases significantly. However, the magnitude of the electric field near the end of the lead is inversely proportional to the impedance of the lead (or shield).

In various embodiments, the pitch of a helix is the width of one complete helix turn, measured along the helix axis. FIG. 8 illustrates the pitch 48 of the ribbon and the pitch 49 of the inner conductor 32. In accordance with some embodiments, the inner conductor 32 can have an average pitch between, and including, five mils (i.e., 5/1000 of inch) and fifty mils (i.e., 50/1000 of inch). In some embodiments, inner conductor 32 may have a maximum pitch of approximately five mils, while in other embodiments the maximum pitch may be more or less. The variation of the pitch in various embodiments can also be a function of wire diameter. For example, if the wire diameter is 3 mils, then the minimum pitch can be slightly larger than 3 mils. If the wire lead is insulated and turn by turn capacitance is not large, then minimum pitch is 3 mils in some embodiments.

In some embodiments, the pitch of the ribbon may be the same as the pitch of the inner conductor 32, larger than the pitch of the inner conductor 32, or smaller than the pitch of the inner conductor 32. FIG. 8 illustrates an embodiment where the pitch 48 of the ribbon is larger than the pitch 49 of the inner conductor 32.

Figure 9:
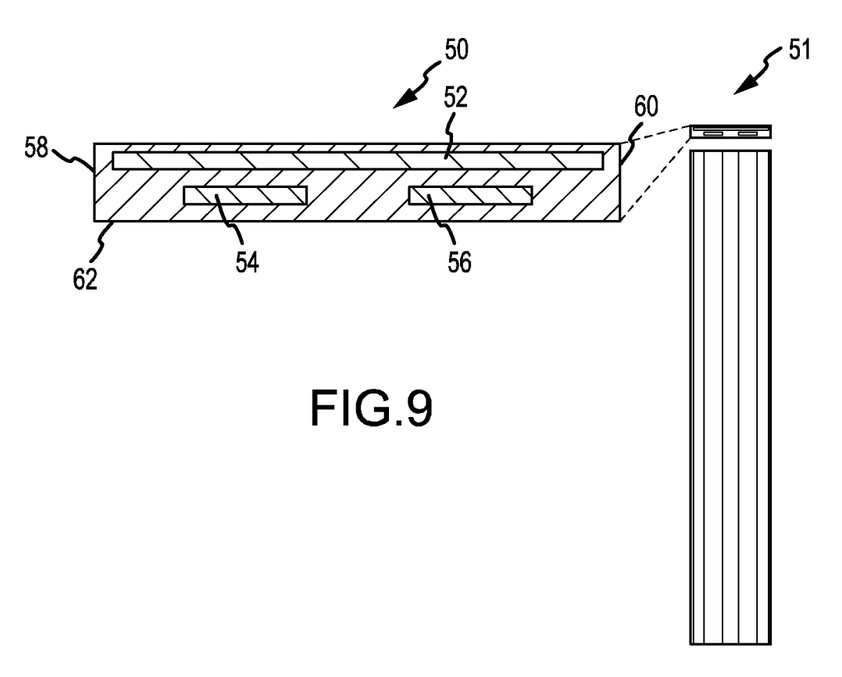
FIG. 9 is a view showing the cross-section of a lead in accordance with another illustrative embodiment.

FIG. 9 is a view showing the cross-section 50 of an uncoiled lead prior to being coiled in accordance with another embodiment of the present invention. Cross-section 50 is an enlarged, transverse cross-sectional view across the width of the ribbon 51. As shown in FIG. 9, the uncoiled lead 50 includes an outer conductor 52 and a number of inner conductors 54, 56. The outer conductor 52 comprises a shielding conductor that can be used for shielding the inner conductors 54, 56 of the lead 50 from electromagnetic energy during magnetic resonance imaging. The inner conductors 54, 56, in turn, comprise conductors for use in transmitting energy through the lead 50 for providing therapy and/or delivering energy to a treatment site within the patient, or for sensing electrical activity occurring within the patient's body.

In some illustrative embodiments, the width of the shielding conductor 52 can be relatively large in comparison to the width of the inner conductors 54, 56. As shown in FIG. 9, for example, the width of the outer conductor 52 may span all or a substantial portion of the width of the lead 50, as defined by sides 58 and 60.

Dimensions of various embodiments depend on a number of variables. A range of wire width in some embodiments can be between approximately 2-6 mils. In some embodiments, the wire thickness can be between approximately 1-3 mils. The shield width, in some embodiments, can be between approximately 4-12 mils. However, in some cases, the shield width can depend on the number of conductors. The shield thickness in some embodiments can be between approximately 1-3 mils. In some embodiments, the shield to edge distance can be less than 1 mil. In other embodiments, the wire width, wire thickness, shield width, shield thickness, and/or shield to edge distance may be smaller or larger than the ranges provided above.

Figure 10:
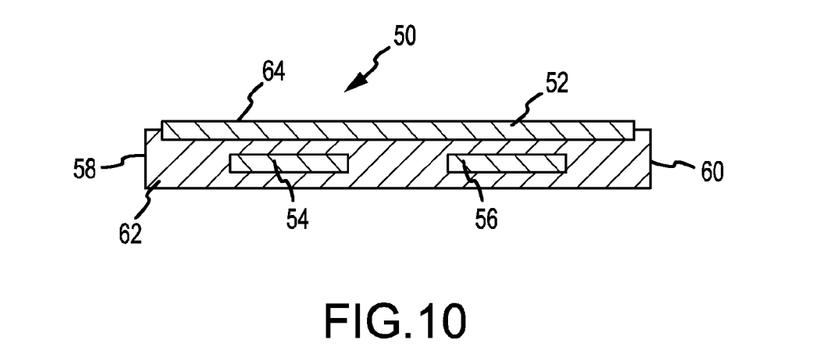
FIG. 10 is a view showing the cross-section of a lead in accordance with another illustrative embodiment.

An insulator material 62 may surround the inner conductors 54, 56 and the outer conductor 52, as shown. In another embodiment depicted in FIG. 10, at least a portion of the outer surface 64 of the outer conductor 52 is not insulated, thus exposing a portion of the outer conductor 52 to the surrounding tissue in the body.

Figure 11:
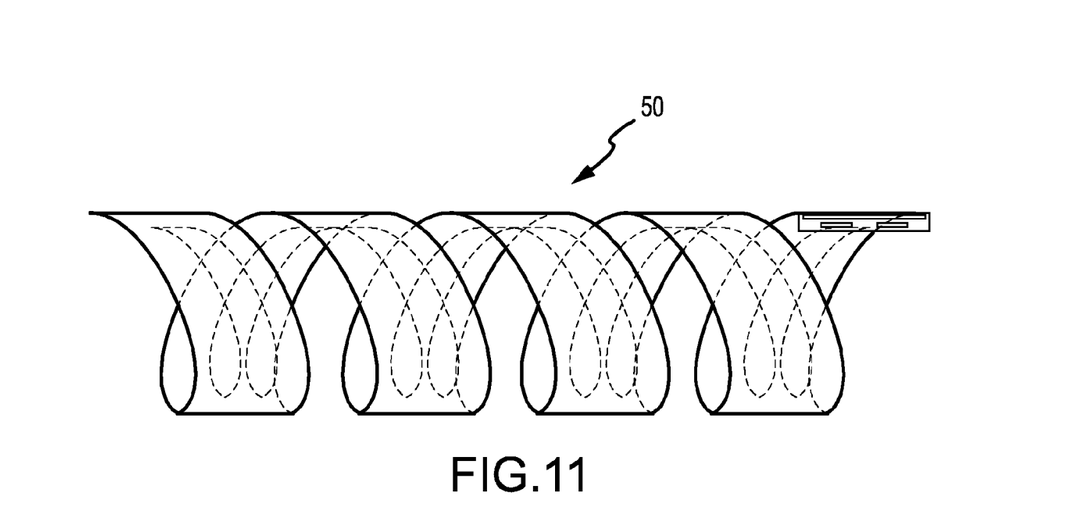
FIG. 11 is a view showing the illustrative lead of FIG. 9 having a helix configuration along its length.

FIG. 11 is a view showing the illustrative lead 50 of FIG. 9 having a helix configuration along its length similar to that discussed above with respect to the embodiment of FIG. 2.

Figure 12:
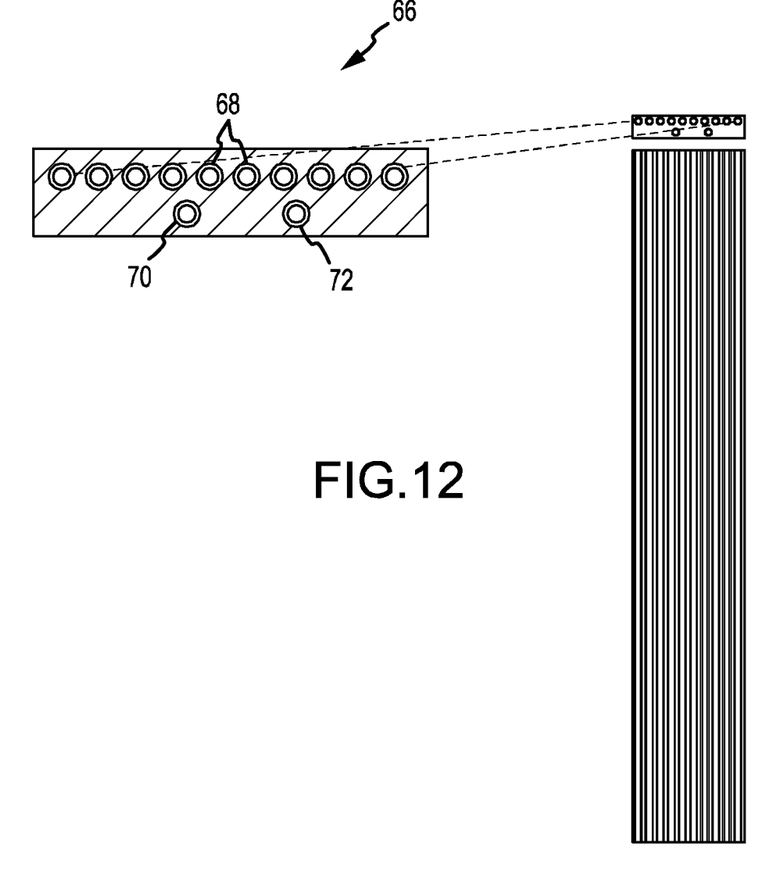
FIG. 12 is a view showing the cross-section of a lead in accordance with another illustrative embodiment.

FIG. 12 is a view showing the cross-section of a lead 66 in accordance with another embodiment of the present invention. As shown in FIG. 12, the lead 66 includes a number of outer conductor wires 68 that shield a number of inner conductor wires 70, 72. The outer conductor wires 68 function as shielding conductors that can be used for shielding the inner conductor wires 70, 72 of the lead 66 from electromagnetic energy during magnetic resonance imaging. The inner conductor wires 70, 72, in turn, comprise conductor wires for use in transmitting energy through the lead 66 for providing therapy and/or delivering energy to a treatment site within the patient.

Figure 13:
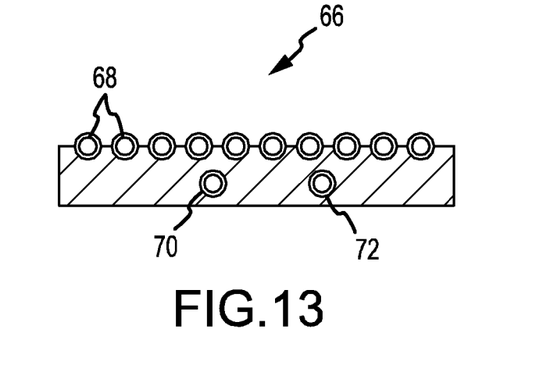
FIG. 13 is a view showing the cross-section of a lead in accordance with another illustrative embodiment.

In the illustrative embodiment of FIG. 12, an insulator material 74 surrounds the inner conductor wires 70, 72 and the outer shielding conductor wires 68. In another embodiment depicted in FIG. 13, at least a portion of the outer surface of the lead 66 is not insulated, thus exposing a portion of the outer conductor wire 68 to the surrounding tissue in the body.

Figure 14:
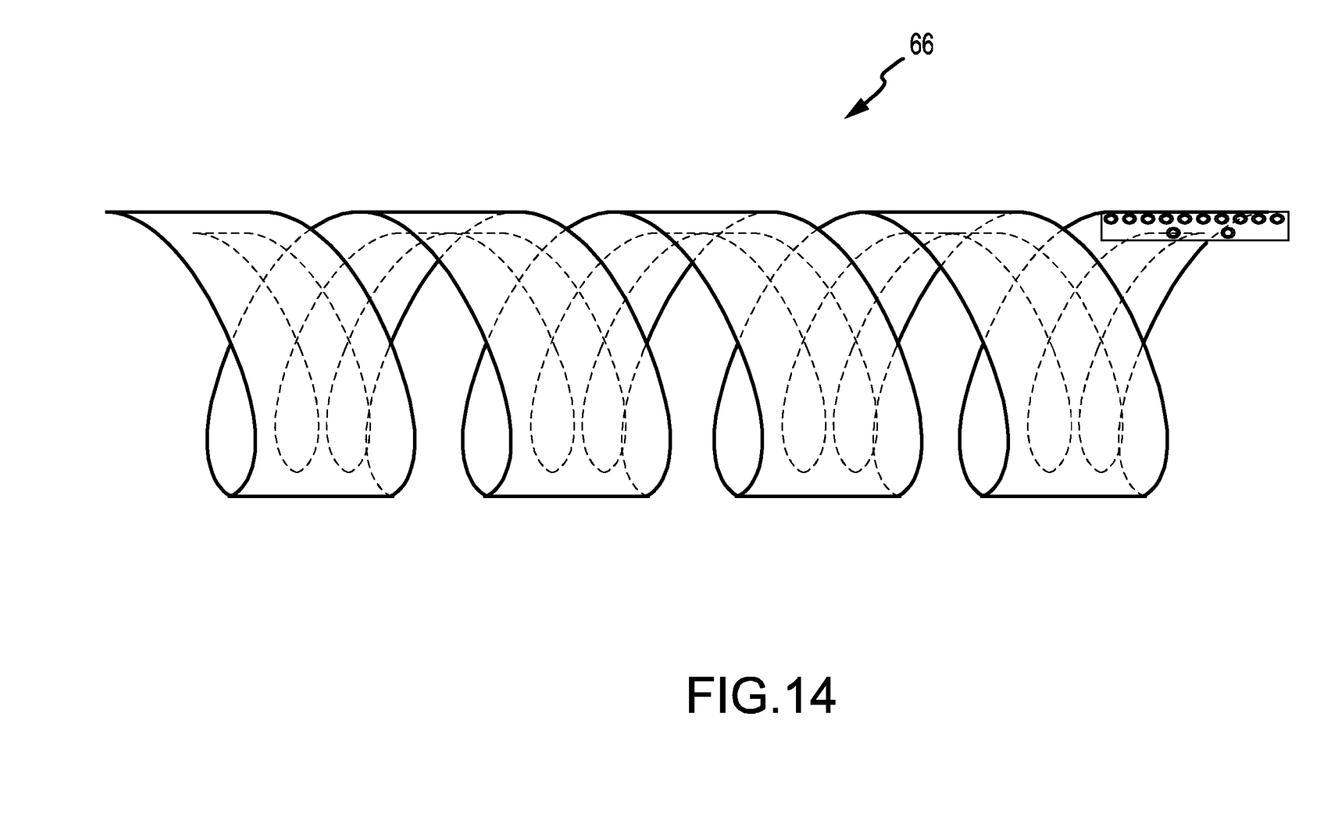
FIG. 14 is a view showing the illustrative lead of FIG. 12 having a helix configuration along its length.

FIG. 14 is a view showing the illustrative lead 66 of FIG. 12 having a helix configuration along its length similar to that discussed above with respect to the embodiment of FIG. 2.

In certain embodiments, the pitch of the shielding and/or the inner conductor can be varied along the length of the lead to alter the impedance characteristics of the shielding and/or lead in a desired manner. For example, different sections of the ribbon shielding can have a high impedance for different RF frequencies depending on the type of MRI device employed. MRI's with different sized magnetic coils often operate at different RF frequencies. However, within a particular MRI device, the RF frequency is typically fixed. For an MRI device having a 1.5 Tesla magnetic coil, for example, the RF frequency is approximately 64 MHz. For an MRI having a 3 Tesla magnetic coil, the RF frequency is approximately 128 MHz. Other RF frequencies are also employed for MRI devices with different magnetic coil strengths.

Figure 15:
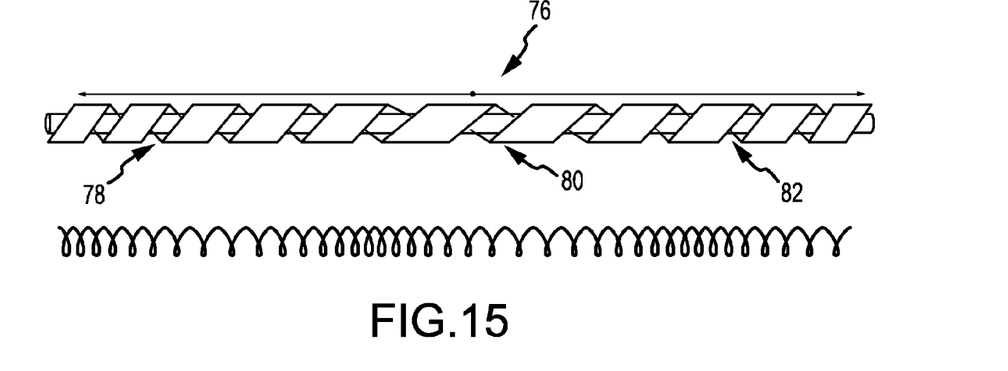
FIG. 15 is a view showing a lead shield and lead having a variable pitch.

In one such embodiment depicted in FIG. 15, for example, a shielding 76 may include various sections 78, 80, 82 that vary in pitch along the length of the lead. In some embodiments, the variable pitch sections 78, 80, 82 of the shielding 76 may correspond to variances in pitch in the electrode conductor for the lead. In other embodiments, the variances in pitch in the shielding 76 may differ from the electrode conductor for the lead. In certain embodiments, for example, the pitch in the shielding 76 may vary whereas the pitch of the inner conductor for the lead is relatively constant.

In some embodiments, the pitch pattern of the ribbon shield is repeated several times along the length of the lead such that the pitch pattern covers a lead length of less than ¼ of the wavelength of the highest frequency of interest. This detuning prevents the lead/shield from approaching the antenna resonance length, thus minimizing the RF energy picked-up on the lead/shield.

Figure 16:
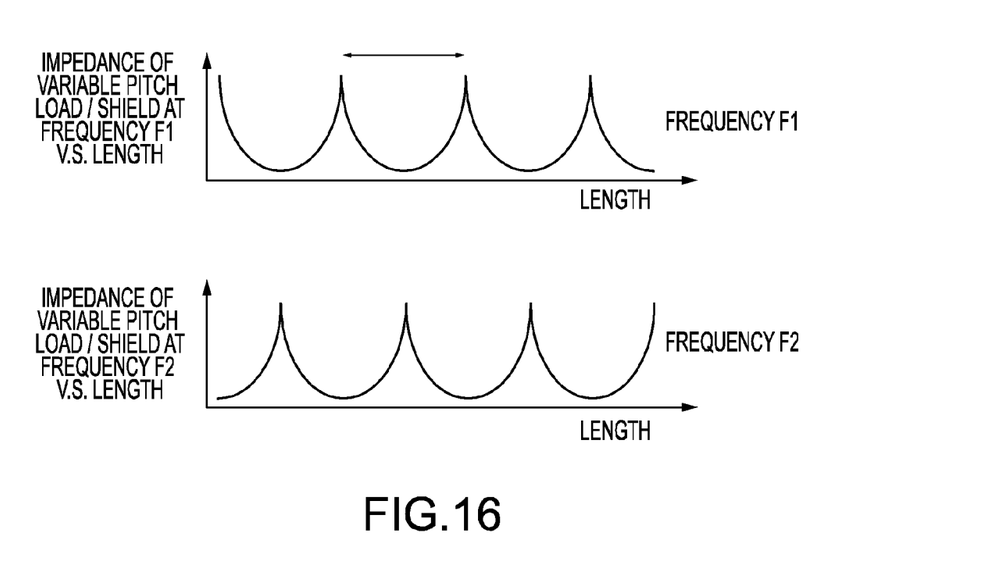
FIG. 16 shows two graphs of the impedance of a variable-pitch lead shield versus the length of the shield at two different MRI frequencies.

FIG. 16 shows two graphs of the impedance of a variable-pitch shield versus the length of the shield at two different RF frequencies F1 and F2. The magnetic field strength of an MRI scanner typically ranges from 0.2-3 Tesla. Accordingly, the range of the RF frequency would be between 8.53 to 128 MHz. As shown in FIG. 16, the locations along the length of the shielding where a relatively high impedance (resonance) occurs depends on the frequency F1, F2 of the RF energy produced by the MRI device.

For example, F1 could be an RF frequency of 64 MHz for a 1.5 T MRI scanner while F2 could be a 128 MHZ for a 3.0 T MRI scanner. Thus, for frequency F1 shown in the top graph, the location along the length of the shielding where an increase of impedance occurs is different than for frequency F2 shown in the bottom graph. This can be seen by a shift in the impedance peaks in the top and bottom graphs shown in FIG. 16.

Figure 17:
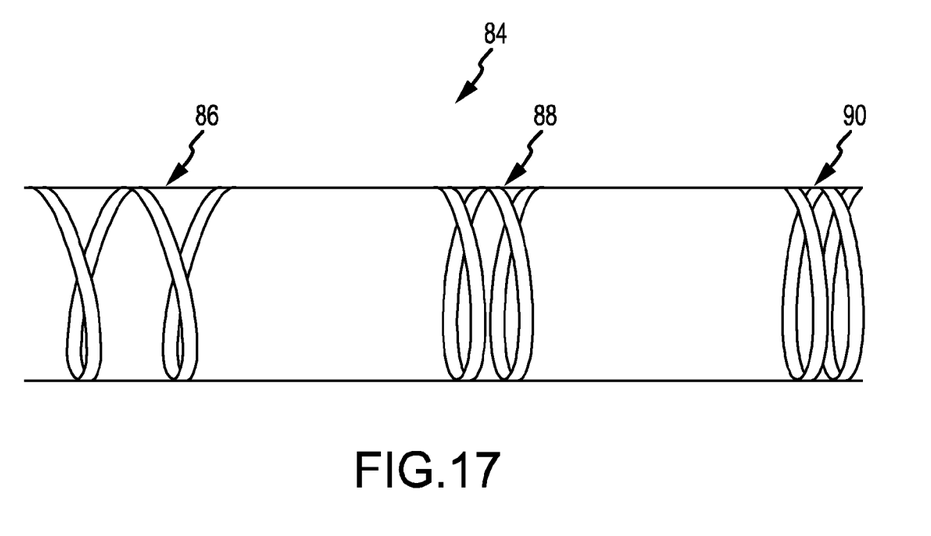
FIG. 17 is a view showing a variable pitch lead in accordance with an illustrative embodiment.

FIG. 17 is a view showing portions of a variable pitch lead 84 in accordance with an illustrative embodiment. For purposes of illustration, the entire lead is not shown in FIG. 17. Various portions of the lead/shielding between the sections 86, 88, 90 are not illustrated in order to more clearly show the variance in pitch between the different sections. As shown in FIG. 17, the lead 84 may include a first section 86, a second section 88, and a third section 90 of a variable inner conductor and/or a variable shielding conductor. The variance of pitch in either the inner conductor or the shielding conductor along each section 86, 88, 90 may follow a particular function, either continuously or discretely.

Figure 18:
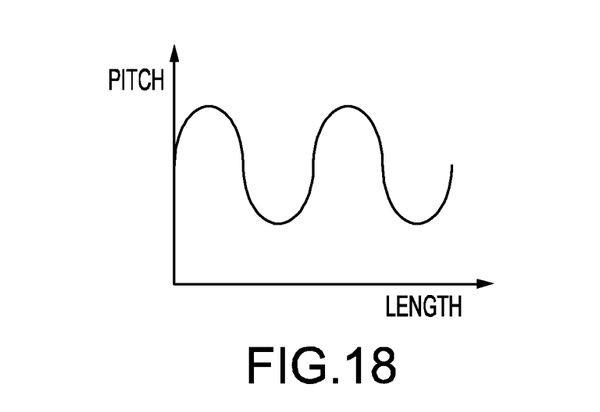
FIG. 18 is a graph showing the pitch of a lead following a sinusoidal function.
Figure 19:
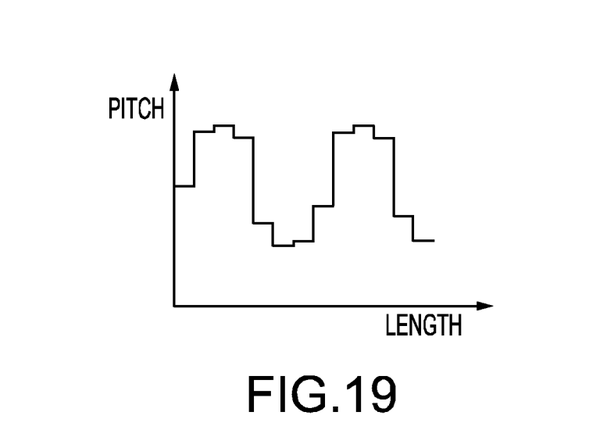
FIG. 19 is a graph showing the pitch of a lead following a modified square-wave function.

As can be further seen in FIG. 18, for example, the pitch of the lead 84 may follow a function that varies sinusoidally along the length of the lead 84. The variance in pitch may follow other functions such as a square wave or other such function. In one alternative embodiment depicted in FIG. 19, for example, the pitch of the lead 84 may follow a modified square-wave function. Other pitch configurations, however, are possible.

In certain embodiments, the width of the shielding conductor for the lead can be varied in order to change the capacitance between turns of the conductive shield within the lead. The changing capacitance results from the distance between adjacent shield conductors being varied. As a result, the lead will have different capacitances between adjacent coil turns and therefore different resonance frequencies.

The resonance frequency of a parallel inductor and capacitor is proportional to $1/2\pi\sqrt{LC}$. Instead of changing the inductance of the lead by changing the pitch, as is done in some embodiments, other embodiments change the parasitic capacitances that exist between adjacent coil turns by changing the width of the shield along the length of the lead. This change in capacitance between adjacent coil turns along the length of the lead can also impart other desired characteristics to the lead, including ease of manufacturing, flexibility, reliability, etc.

Figure 20:
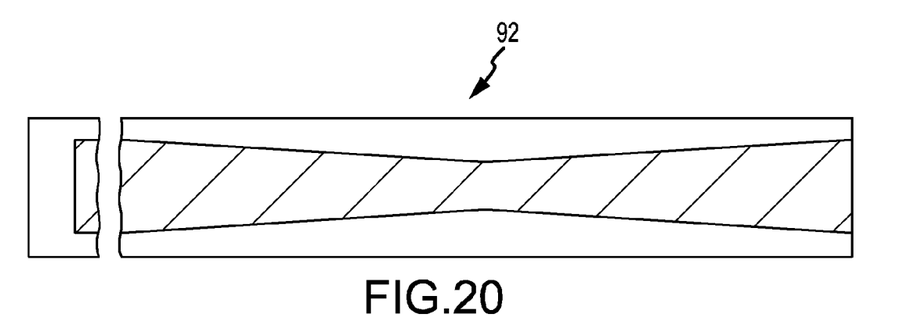
FIGS. 20-22 are views showing several illustrative lead configurations in which the width of the shielding varies along its length.
Figure 21:
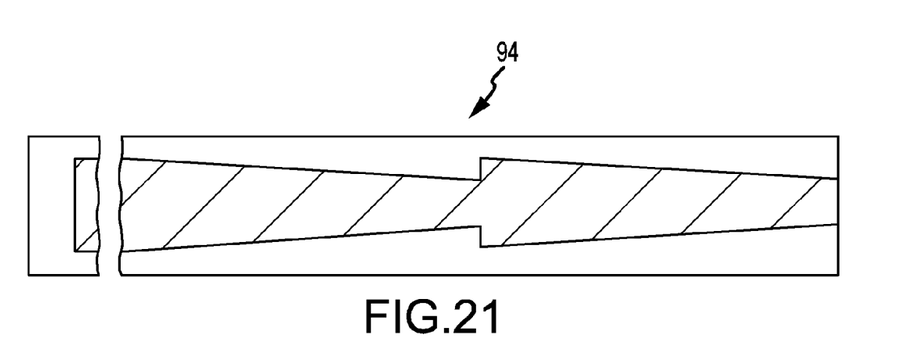
Figure 22:
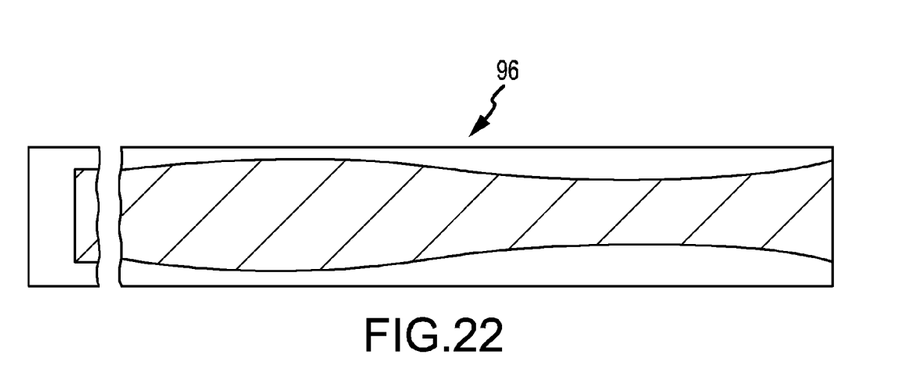

FIGS. 20-22 depict several illustrative lead configurations in which the width of the shielding varies along its length. FIG. 20 shows an illustrative lead 92 having a necked-down configuration. FIG. 21 shows an illustrative lead 94 having an arrowhead configuration. FIG. 22 shows an illustrative lead 96 having an undulating configuration. In each of these embodiments, the changes in width of the shielding varies the resonance frequency along the length of the lead or shielding.

Although the present invention can be used to provide shielding against electromagnetic energy produced during MRI imaging, other applications where the shielding against RF energy is desired are also possible. In certain embodiments, for example, the devices and methods described herein can be used in other environments in which RF noise or other electromagnetic interference is present.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:
1. An implantable medical device, comprising:
a lead having a proximal section and a distal section, wherein the lead includes a lead conductor having a length;
a helically coiled ribbon shield radially surrounding the lead conductor along at least a portion of the length of the lead, the helically coiled ribbon shield including at least one inner ribbon conductor and an outer ribbon conductor disposed about the at least one inner ribbon conductor; and wherein the helically coiled ribbon shield is configured to transfer electromagnetic energy received by the lead during a magnetic resonance imaging procedure to body tissue surrounding the lead.

2. The implantable medical device of claim 1, wherein the lead includes a layer of insulation disposed about at least a portion of the helically coiled ribbon shield.

3. The implantable medical device of claim 1, wherein the outer ribbon conductor has a variable width along the length of the lead.

4. The implantable medical device of claim 3, wherein the variable width includes a necked-down configuration, an arrowhead configuration, or an undulating configuration.

5. The implantable medical device of claim 1, wherein the helically coiled ribbon has a variable pitch along the length of the lead.

6. The implantable medical device of claim 5, wherein the variable pitch of the helically coiled ribbon follows a sinusoidal function or a modified square-wave function.

7. The implantable medical device of claim 1, wherein an impedance path of the helically coiled ribbon shield along the length of the lead is higher than the impendence path from the helically coiled ribbon shield to body tissue surrounding the lead.

8. The implantable medical device of claim 1, wherein the outer ribbon conductor of the helically coiled ribbon includes a plurality of wire conductors.

9. The implantable medical device of claim 1, wherein the outer ribbon conductor of the helically coiled ribbon shield includes a ribbon-shaped outer conductor.

10. The implantable medical device of claim 1, wherein a portion of the outer ribbon conductor is not insulated.

11. The implantable medical device of claim 1, wherein the lead includes a low impedance insulation near the proximal section and the distal section of the lead, the insulation adapted to dissipate electromagnetic energy into the body tissue along the length of the lead for reducing energy transfer of the electromagnetic energy to an electrode attached to the lead.

12. The implantable medical device of claim 1, wherein a width of the helically coiled ribbon shield varies along a length of the shield.

13. An implantable medical device, comprising:
a lead having a proximal section coupled to a pulse generator, a distal section implanted within a heart of a patient, and a length, wherein the lead is configured to convey electrical signals between the heart and the pulse generator through an inner conductor; and
a helically coiled shielding ribbon radially disposed about at least a portion of the inner conductor, the helically coiled shielding ribbon including at least one conductor with a width that varies along the length of the helically coiled shielding ribbon, wherein the width of the helically coiled shielding ribbon is greater than a width of the inner conductor.

14. The implantable medical device of claim 13, wherein the at least one conductor of the helically coiled shielding ribbon includes a plurality of wire conductors.

15. The implantable medical device of claim 13, wherein the inner conductor has a helix-like shape with a continuously varying conductor pitch forming one or more high impedance points along the length of the lead at one or more frequencies.

16. The implantable medical device of claim 13, wherein the helically coiled shielding ribbon has a pitch that continuously varies.

17. The implantable medical device of claim 16, wherein the pitch of the helically coiled shielding ribbon follows a sinusoidal function or a modified square-wave function.

18. A medical lead, comprising:
an inner conductor configured to convey electrical signals between a distal section and a proximal section of the lead; and
a ribbon shield formed in a helix-like shape radially surrounding at least a portion of the inner conductor, the ribbon shield including a ribbon shield outer conductor and a ribbon shield inner conductor, and having a pitch that varies along a length of the lead.

19. The lead of claim 18, wherein the variable pitch of the ribbon shield continuously varies forming one or more high impedance points along the length of the lead.

20. The lead of claim 18, wherein a pitch of the inner conductor continuously varies along the length of the lead.

21. The lead of claim 20, wherein the pitch of the inner conductor follows a sinusoidal function or a modified square-wave function.

* * * * *